United States Patent [19]

Liquido et al.

[11] Patent Number: 6,019,964
[45] Date of Patent: Feb. 1, 2000

[54] **ATTRACTANTS FOR *BACTROCERA LATIFRONS*(HENDEL)**

[75] Inventors: Nicanor J. Liquido, Honolulu, Hi.; Roy T. Cunningham, Crestone, Colo.; Grant T. McQuate, Kea'au, Hi.; Robert A. Flath, Kensington, Calif.

[73] Assignee: The United States of America as represented by the Secretary of Agriculture, Washington, D.C.

[21] Appl. No.: 09/120,521

[22] Filed: Jul. 21, 1998

[51] Int. Cl.[7] .......................... A01N 65/00; A01N 31/04; A01M 1/10; A01M 1/20
[52] U.S. Cl. .................. 424/84; 424/195.1; 514/547; 514/729; 43/107
[58] Field of Search .................... 424/84, 195.1; 514/547, 729; 43/107

[56] References Cited

U.S. PATENT DOCUMENTS 4,877,607 10/1989 McGovern et al. ....................... 424/84

OTHER PUBLICATIONS

Flath, Robert A. et al., "Alpha–Ionol as Attractant for Trapping *Bactrocera latifrons* (Diptera: Tephritidae)," Journal of Economic Entomology, vol. 87, No. 6, pp. 1470–1476, Dec. 1994.

M. Beroza and N. Green, "Materials Tested as Insect Attractants," *Agriculture Handbook No. 239*, USDAARS, Washington, D.C. p. 111 (1963).

*Primary Examiner*—John Pak
*Attorney, Agent, or Firm*—M. Howard Silverstein; John D. Fado; Margaret A. Connor

[57] ABSTRACT

Compositions and combinations of alpha-ionol and cade oil are effective attractants for *Bactrocera latifrons* (Hendel) fruit flies. By attracting adult males to field traps or baits, the attractants provide a means for detecting, surveying, monitoring, and controlling this agricultural pest.

14 Claims, 9 Drawing Sheets

ATTRACTANTS FOR *BACTROCERA LATIFRONS* (HENDEL)

BACKGROUND OF THE INVENTION

1. Field of the Invention

The present invention relates to synthetic insect attractants and use thereof for insect detection and control. More particularly, the invention relates to a composition or combination of alpha-ionol and cade oil as attractants for the tephritid fruit fly *Bactrocera latifrons* (Hendel), and use thereof to detect, survey, monitor, and/or control this pest.

2. Description of the Art

Tephritid fruit flies from tropical and subtropical regions of the world pose a constant invasion threat to both agricultural and urban regions of the continental United States. If tephritid fruit flies were allowed to invade and infestations were to become established in the continental United States, the estimated cost would be hundreds of millions of dollars in direct control costs and billions of dollars in commodity treatment costs and/or embargoes and lost export markets. Thus, fruit fly invasions must be quickly detected, and the geographical extent of such infestation must be precisely delineated prior to and throughout the accompanying eradication control programs.

The fruit fly, *Bactrocera latifrons* (Hendel) [Diptera:Tephritidae], formerly *Dacus latifrons* (Hendel), is also known by the common names, Solanaceous fruit fly and Malaysian fruit fly. It is primarily a pest of Solanaceous crops, e.g., pepper, tomato, eggplant, and occasionally hosts on Cucurbitaceous plants. It invaded Hawaii from the Far-East, and is now well established as a new pest throughout the Hawaiian Islands. It poses a threat of an invasion of the continental United States. *Bactrocera latifrons* is also a pest of commercial significance in parts of Asia.

U.S. Pat. No. 4,877,607 describes specific cyclohexyl and cyclohexenyl alcohols and ketones that are attractants for *Bactrocera latifrons* males. Exemplary compounds include alpha-ionol, β-ionol, and α-methyl-α-ionol. The only compound of the patent that is used commercially for detection programs is alpha-ionol. Field experiments have demonstrated that alpha-ionol alone does attract male *Bactrocera latifrons*, however, it is far inferior in attractancy and efficacy compared to lures of other tephritid pests, and is only marginally effective as a detection lure for *Bactrocera latifrons* invasions. Thus, there is a current need for a more potent lure for *Bactrocera latifrons*.

Beroza and Green compiled the results of a laboratory screening study of over 4,000 materials tested as insect attractants against 10 insect species. They report attractiveness of cade oil to *B. dorsalis* or *B. cucurbitae* in laboratory screening tests using outdoor cages. No attractiveness of cade oil was found for the other 8 insect species tested, which included the Mediterranean fruit fly and Mexican fruit fly. (See Beroza and Green, *Materials Tested as Insect Attractants*, Agriculture Handbook No. 239, USDA ARS, Washington, D.C., page 111 (1963)).

SUMMARY OF THE INVENTION

We have discovered that compositions or combinations of the compounds, alpha-ionol and cade oil, are highly effective attractants for *Bactrocera latifrons* (Hendel) males and provide a means for detection, surveying, monitoring, delimitation of infestation, suppression, and control of *Bactrocera latifrons* populations. Early detection of *Bactrocera latifrons* invading new areas, such as the continental United States, would provide opportunity to detect populations at an early stage of invasion and provide more ready eradication of infestations of this agricultural quarantined pest. Although alpha-ionol alone, has been previously noted as an attractant for *Bactrocera latifrons* males, surprisingly, we have found that the addition of cade oil acts as a powerful synergist of alpha-ionol. As shown in Example 1, below, and FIG. 1, the attraction of *Bactrocera latifrons* males to the combination of alpha-ionol and cade oil is over 3.6-fold and 7.4-fold greater than the attraction of alpha-ionol alone and cade oil, alone, respectively. Thus, the invention fulfills a long felt need for a more potent lure for *Bactrocera latifrons* males.

Compositions or combinations of alpha-ionol and cade oil produce vapor blends or vapor mixtures of the compounds which function as highly effective attractants for *Bactrocera latifrons*. In one embodiment, the attractant alpha-ionol and cade oil is provided by a mixture of the two compounds. In another embodiment, a vapor blend is provided by a combination of alpha-ionol and cade oil wherein the two compounds are positioned in sufficient proximity to one another to form a volatilized blend.

The attractant compositions or combinations of the invention provide a means for detection, surveying, monitoring, delimitation of infestation, suppression, and control of *Bactrocera latifrons* populations. Because the attractants attract males of the species, they can be used for annihilation of *Bactrocera latifrons* males.

The mixture or combination of alpha-ionol and cade oil may be used as male lures and in conjunction with any type of traps and controlled release devices known in the art. Thus, the invention is also directed to lures wherein a mixture or combination of alpha-ionol is held in a dispenser means which releases the mixture or combination so as to form the attractant vapor blend. The invention is further directed to trapping systems which include trapping means and an effective attractant amount of a mixture or combination of alpha-ionol and cade oil.

An important feature is that the invention provides an effective lure for use to detect and monitor the *Bactrocera latifrons* to determine the presence of the pest and whether control measures are needed. Thus, the composition offers an important tool in an integrated pest management program for control of this pest. By monitoring pest populations with traps baited with the composition, the numbers of insecticide applications can be reduced while increasing the effectiveness of control because insecticides are only applied when the *Bactrocera latifrons* is present.

Further, when used in combination with a control agent for the *Bactrocera latifrons*, such as a drowning solution, a pesticide or biological control agent, the composition can be used as a direct control agent by attracting *Bactrocera latifrons* males to a trap and incapacitating the insects so that they are not able to fertilize the females.

In sum, the novel attractants of the invention provide a sensitive tool for the detection of the *Bactrocera latifrons* and provide a means for population control and population density estimation of this pest. The usefulness in eliciting a behavioral response when applied to a locus of *Bactrocera latifrons* males suggests the following economic applications: (1) the detection of infestation outbreaks or rapid population buildups; (2) the monitoring of existing adult populations in order to predict future infestation levels for scheduling treatment the following year with larval insecticides or for treatment of adult flies in the current year with conventional pesticides or other control agents, (3) surveying to determine if this insect is established in a particular geographical location, and (4) the control of reproduction in adult populations by attracting a demographically significant portion of the male population for subsequent destruction.

In accordance with this discovery, it is an object of the invention to provide attractants for *Bactrocera latifrons* (Hendel).

Another object of the invention is the provision of the attractants as detection, surveying, monitoring, delimitation of infestation, suppression and/or control agents for the *Bactrocera latifrons*.

A further object of the invention is the provision of a *Bactrocera latifrons* attractant for use with control agents, including drowning solutions, insecticides, biological control agents, or other toxicants, to attract and combat this pest.

Other objects and advantages of the invention will become readily apparent from the ensuing description.

BRIEF DESCRIPTION OF THE DRAWINGS

FIG. 2a shows the catch of *Bactrocera latifrons* males at Jackson traps baited with alpha-ionol only (0.6 ml), cade oil only (0.6 ml), or a 12:1 mix of alpha-ionol:cade oil (0.6 ml:0.05 ml).

FIG. 2b shows the catch of *Bactrocera latifrons* males at Jackson traps baited with alpha-ionol only (0.6 ml), cade oil only (0.6 ml), or a 6:1 mix of alpha-ionol:cade oil (0.6 ml:0.1 ml).

FIG. 2c shows the catch of *Bactrocera latifrons* males at Jackson traps baited with alpha-ionol only (0.6 ml), cade oil only (0.6 ml), or a 3:1 mix of alpha-ionol:cade oil (0.6 ml:0.2 ml).

FIG. 2d shows the catch of *Bactrocera latifrons* males at Jackson traps baited with alpha-ionol only (0.6 ml), cade oil only (0.6 ml), or a 1:1 mix of alpha-ionol:cade oil (0.6 ml:0.6 ml).

FIG. 2f shows the catch of *Bactrocera latifrons* males at Jackson traps baited with alpha-ionol only (0.6 ml), cade oil only (0.6 ml), or a 1:3 mix of alpha-ionol:cade oil (0.6 ml:1.8 ml).

FIG. 3a shows the catch of *Bactrocera latifrons* males at Jackson traps baited with alpha-ionol only (0.6 ml), cade oil only (0.6 ml), or a 6:1 mix of alpha-ionol:cade oil (0.6 ml:0.1 ml).

FIG. 3b shows the catch of *Bactrocera latifrons* males at Jackson traps baited with alpha-ionol only (0.6 ml), cade oil only (0.6 ml), or a 3:1 mix of alpha-ionol:cade oil (0.6 ml:0.2 ml).

FIG. 3c shows the catch of *Bactrocera latifrons* males at Jackson traps baited with alpha-ionol only (0.6 ml), cade oil only (0.6 ml), or a 1:1 mix of alpha-ionol:cade oil (0.6 ml:0.6 ml).

FIG. 3e shows the catch of *Bactrocera latifrons* males at Jackson traps baited with alpha-ionol only (0.6 ml), cade oil only (0.6 ml), or a 1:3 mix of alpha-ionol:cade oil (0.6 ml:1.8 ml).

DETAILED DESCRIPTION OF THE INVENTION

Figure 1:
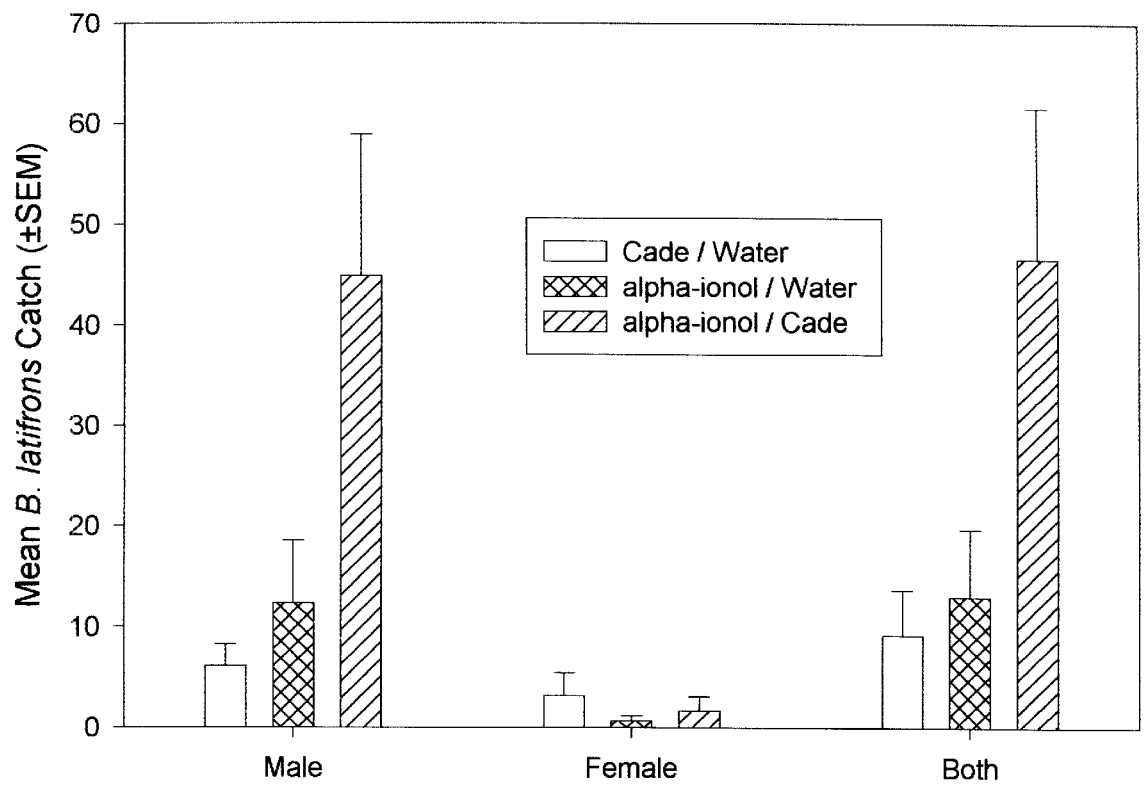
FIG. 1 shows the catch (mean *Bactrocera latifrons* catch±standard error of the mean (SEM)), 24 hours after release, of sterile *Bactrocera latifrons*, in yellow-bottom plastic dome traps holding wicks treated with cade oil alone (0.5 ml), alpha-ionol alone (0.5 ml), or with 0.5 ml alpha-ionol and 0.5 ml cade oil at opposite ends of the wick.

The invention comprises attractant compositions or combinations of the compounds, alpha-ionol and cade oil, which function as effective attractants for *Bactrocera latifrons* (Hendel) males and provide a means for detection, surveying, monitoring, delimitation of infestation, suppression, and control of *Bactrocera latifrons* populations. Because the attractants attract males of the species, they fulfill an important need of annihilation of *Bactrocera latifrons* males.

The compounds for producing the attractants of the invention are commercially available. Alpha-ionol [4-(2,6,6- trimethyl-2-cyclohexen-1-yl)-3-buten-2-ol; CA Registry No. 25312-34-9] is a colorless liquid, insoluble in water, soluble in alcohol, with a boiling point about 127° C. A procedure for synthesizing alpha-ionol is presented in U.S. Pat. No. 4,877,607, which is hereby incorporated by reference. Cade oil is a product of the distillation of the wood, e.g., *Juniperus oxycedrus L.*, is a generally dark brown to black liquid, slightly soluble in water, and soluble in alcohol. Alpha-ionol and cade oil are liquid over the range of temperature at which lures would be used to attract fruit flies and can be readily mixed together without the use of additives or solvents.

Compositions or combinations of alpha-ionol and cade oil produce vapor blends or vapor mixtures of the compounds which function as effective attractants for *Bactrocera latifrons*. In one embodiment, the vapor blend of alpha-ionol and cade oil is provided by a mixture of the two compounds. In another embodiment, the vapor blend is provided by a combination of alpha-ionol and cade oil wherein the two compounds are positioned in sufficient proximity to one another to form a volatilized blend.

In practice, the attractants are used as lures or trap baits or otherwise applied to a locus of *Bactrocera latifrons*, that is, an area where the insects are present or may occur. The two-component attractant of alpha-ionol and cade oil are formulated or presented so as to provide an effective attractant amount of the mixture or combination of the odor blend of the two chemicals. An effective amount is defined as that quantity of alpha-ionol and cade oil emitted by a formulation or dispenser that attracts *Bactrocera latifrons* males to the location of a bait at a rate significantly higher than males are attracted to a nonbaited location. Attracted flies respond to the combination of alpha-ionol and cade oil present simultaneously in air and they move upwind towards the source of the bait.

The broad range of volumetric ratios of the compounds in the composition that is an effective attractant for *Bactrocera latifrons* males is about 12:1 to 1:3 (alpha-ionol:cade oil). We have found that ratios of about 1:1 to 1:3 (alpha-ionol:cade oil) have longer duration effectiveness. Amounts of about 0.5 ml to 5 mls of the mixture are effective; 0.65 to 2 mls of the mixture can be used. As discussed below, various factors including environmental factors and fruit fly population density can influence the actual number of fruit flies attracted. The amounts of alpha-ionol and cade oil in a particular set of circumstances that will provide release rates within an effective range can be determined by dose response field tests as described in Examples 1–3, below. The choice of a particular methodology in detection programs in any particular instance can be decided by the program manager.

Alpha-ionol and cade oil may be used as lures in conjunction with any type of traps and controlled-release devices known in the art. When used as a detection, survey, or monitoring agent, traps are baited with the attractant of the invention and the catch tabulated to determine size and location of infestation. Economic use of appropriate control agents can then be determined. When used for control of *Bactrocera latifrons*, the attractants are used in conjunction with control agents as discussed in detail below.

The invention finds particular use as a substitute from alpha-ionol alone in detection programs such as in California. Use of the invention attractants considerably improves the detection of invading or incipient populations of *Bactrocera latifrons*. Exemplary of such detection systems is use of mixtures of alpha-ionol and cade oil on cotton wicks or use of the compounds at each end of cotton wicks and placement in Jackson traps, as described in Examples 1–3, below. Conventional procedures for detection of tephritid fruit flies are as follows: the traps are set out at a density of about 1 to 10 per square mile and serviced once a week, with recharging each month. The choice of a particular methodology, however, in detection programs in any particular instance would depend on the program manager.

Lures. It is envisioned that the attractants of the invention would be useful in detecting, surveying, monitoring, or controlling *Bactrocera latifrons* fruit flies when used as a lure. A lure includes a dispenser means which contains a mixture of alpha-ionol and cade oil or which contains separately alpha-ionol and cade oil, which provide the attractant vapor blend. For purposes of this invention, a dispenser means is defined as any means which both (a) contains or holds the unvolatilized compounds or mixture used to produce the vapor blend and (b) releases the compound or compounds in the vapor phase to form the vapor blend.

A dispensing means may take several forms, but, in general, a dispensing means includes an absorbent material such as cotton, paper or clay which both holds and releases alpha-ionol or cade oil separately or as a mixture. Other dispensers include those that comprise a reservoir for holding an amount of a compound either within a space or a polymeric matrix, with the release into the atmosphere controlled by a permeable wall or membrane or by a small opening surrounded by an impermeable wall or membrane. Further examples of dispensers include polymer caps, bubbles, hollow fibers, hollow tubes or tubing which release compounds through the walls, capillary tubing which release compounds out of an opening in the tubing, polymeric blocks of different shapes which release compounds out of the polymer matrix, membrane systems which hold the chemicals within an impermeable container and release them through a measured permeable membrane, and combinations of the foregoing. Examples of other dispensing means are polymer laminates, polyvinyl chloride pellets, microcapillaries, and Shunitzu rope. Another dispensing means includes using microencapsulation techniques to encapsulate each compound used to produce the vapor blend.

In one embodiment, alpha-ionol and cade oil are formulated as a mixture and placed in the dispensing means. In another embodiment, alpha-ionol and cade oil are provided separately, but in combination, wherein the two compounds are positioned in sufficient proximity to one another to form a vapor blend. The two compounds may be placed at separate locations on a single dispenser as discussed in the Examples, below, or may be provided in separate dispensers, wherein the two dispensers are placed in sufficient proximity to one another to form a volatilized blend of the two compounds in the surrounding atmosphere. The first and second dispensers may optionally be attached or fused to form one device or unit that releases the two compounds to form the vapor blend.

Controlled release of the compounds may also be affected in part through the addition of an extender such as mineral oil, which will reduce the rate of volatilization of the odorants out of the dispenser. The bait may also contain additives, such as toxicants.

Factors such as fruit fly species present, fruit fly population density, and environmental factors influencing fruit fly behavior (e.g., temperature, wind velocity, rain, time of day and seasonality) will influence the response of the fruit flies to the attractants of the invention and the actual number of fruit flies attracted. The amounts of alpha-ionol and cade oil in a particular set of circumstances that will provide release rates within an effective range can be readily determined by dose response field tests as described in Examples 1–3, below.

Control agents may also be added to provide poisoned baits, as discussed in detail below. Other compounds and materials may be added to a formulation, lure, bait or trap provided they do not substantially interfere with the attractancy of the attractants of the invention. Whether or not an additive substantially interferes with the attractant activity can be determined by standard test formats, involving direct comparisons of efficacy of the attractants of the invention without an added compound and the attractants of the invention with an added compound. Reductions in attractancy, such as reduced captures of fruit flies in traps baited with the attractant with the additive, may be determined with standard statistical analyses.

Means for Controlling *Bactrocera latifrons* Fruit Flies. The attractants of the invention are useful for control of *Bactrocera latifrons* fruit flies when used in concert with means for controlling the flies. Control of fruit flies may be carried out as known in the art, including (a) by capturing the flies in traps, (b) by capturing flies in a trap and killing the flies, for example by means of a drowning solution (c) by attracting the flies to suitable substrates and subsequently or simultaneously exposing the flies to insecticides, toxicants, or chemosterilants, (d) by use of pathogens. An effective amount of a control agent is used, that is, an amount that is lethal for an exposed insect or at least sublethal but sufficient to incapacitate the insect in regard to mating activity. Control agents useful in this invention are those which will not adversely affect the attractiveness of the attractants of the invention. Insecticides can be used in traps baited with the attractant, thereby minimizing the dissemination of the insecticide. A variety of matrix materials may also be employed as a carrier for the control agent. The invention finds use for annihilation of male *Bactrocera latifrons* fruit flies.

Illustrative of the insecticides which may be used with the attractants of the invention are naled, also known as dibrom or 1,2-dibromo-2,2-dichloroethyl dimethyl phosphate, and malathion, also known as [(dimethoxyphosphinothioyl)thio] butanedioic acid diethyl ester.

Trapping Systems. The attractants of the invention may be used as detecting agents, surveying agents, monitoring agents, or control agents for the *Bactrocera latifrons* (Hendel). Conveniently, the attractants are dispensed within a trapping means to attract and trap fruit flies. A trapping system for monitoring or controlling *Bactrocera latifrons* includes a trapping means, and a dispenser means located within the trapping means which provides an effective attractant amount of a vapor blend of vapor of alpha-ionol and cade oil. A trapping means is any device for catching insects, particularly, fruit flies. These include for example, the McPhail trap and Jackson trap. Alpha-ionol and cade oil may be presented as a mixture or separately dispensed within the trap. The lure, bait or trap may optionally contain additional materials that aid in the capture and killing of attracted flies, such as a drowning solution and/or toxicant, as long as such additives do not substantially interfere with the attractiveness of the attractants of the invention.

For traps wherein control is carried using a drowning solution, the drowning solution may optionally contain additional materials that aid in the capture and killing of attracted flies, such as detergents or dyes, as long as such additives do not substantially interfere with the attractiveness of the attractants of the invention.

For traps in which attracted fruit flies are killed by a toxicant or insolation, other formulation methods may be used as known in the art.

Kits and packaged attractants. The invention is also directed to kits. In one aspect the kit includes a trap and a lure for use within the trap and which provides the attractant vapor blend. A bait kit may provide alpha-ionol and cade oil packaged as a mixture or packaged in one or more dispensers for producing a volatilized blend of the two components when the components are released.

EXAMPLES

The following examples are intended only to further illustrate the invention and are not intended to limit the scope of the invention which is defined by the claims.

Example 1

The following example describes field tests assessing the attractancy of alpha-ionol alone, cade oil alone, and the invention (alpha-ionol plus cade oil).

Materials and Methods. Cotton wicks (2.5 cm long by 1.0 cm diameter) were placed inside, suspended from the top of yellow-bottom plastic dome traps (Biosys, Inc., Palo Alto, Calif.) (McPhail-type traps) holding 100 ml of distilled water with 2 drops of TWEEN 20 (ICN Biomedicals, Aurora, Ohio) added, which functions as a drowning solution. Wicks were treated with either 0.5 ml of alpha-ionol (Bedoukian Research, Inc., Danbury, Conn.), 0.5 ml cade oil (Penta International Corporation, Livingston, N.J.), or with 0.5 ml alpha-ionol and 0.5 ml cade oil at opposite ends of the wick. Five traps of each treatment were set out in a random complete block design in a macadamia nut orchard, near Hilo, Hi. With this experimental design, one trap of each treatment was set out in each of 5 rows, with the order of the treatments in each row randomized. One box of about 500, 7–11 day old *Bactrocera latifrons* adults was released below each trap in the grid. The same test was conducted on Nov. 3–4, 1994, Nov. 21–22, 1994 and Jan. 9–10, 1995, making a total of three repetitions.

Results. The average trap catch results are summarized in FIG. 1. There was a significant difference among treatments in male catch ($F=19.32$, $df=2,40$; $P<0.0001$), and in total (male plus female) catch ($F=17.06$; $df=2,40$; $P<0.0001$) but not in female catch ($F=1.98$; $df=2,40$; $P=0.15$). For both male catch and total catch, catch was significantly greater in the alpha-ionol+cade oil treatment than in the other two treatments. Average male catch in traps baited with alpha-ionol+cade oil (45.0) averaged over 3.6 times greater than in traps baited with alpha-ionol alone (12.3). Average total catch in traps baited with alpha-ionol+cade oil (46.7) averaged over 3.5 times greater than in traps baited with alpha-ionol alone (13.0). For male catch, female catch, and total catch, there were no significant differences between catch at traps baited with alpha-ionol alone and traps baited with cade oil alone.

Example 2

The following example describes field tests assessing the attractancy of alpha-ionol alone, cade oil alone, and the invention (alpha-ionol plus cade oil).

Materials and Methods. On Sep. 23, 1996, cotton wicks (3.8 cm long by 1.0 cm diameter) were treated with mixtures prepared with different proportions of alpha-ionol (Bedoukian Research, Inc., Danbury, Conn.) and cade oil (Penta International Corporation, Livingston, N.J.). The knockdown pesticide, dibrom (Dibrom Concentrate, Valent USA Corporation, Walnut Creek, Calif.; ingredient name: naled), was added to each mixture so that each treated wick would have at least 0.1 ml dibrom. The following proportions (alpha-ionol:cade oil) were prepared, with quantity added to individual wicks also indicated:

(1) [0:1] 0.6 ml cade oil+0.1 ml dibrom;
(2) [1:0] 0.6 ml alpha-ionol+0.1 ml dibrom;
(3) [12:1] 0.6 ml alpha-ionol+0.05 ml cade oil+0.1 ml dibrom;
(4) [6:1] 0.6 ml alpha-ionol+0.1 ml cade oil+0.1 ml dibrom;
(5) [3:1] 0.6 ml alpha-ionol+0.2 ml cade oil+0.1 ml dibrom;
(6) [1:1] 0.6 ml alpha-ionol+0.6 ml cade oil+0.1 ml dibrom;
(7) [1:3] 0.6 ml alpha-ionol+1.8 ml cade oil+0.1 ml dibrom.

In addition to these seven treatments, an eighth treatment was prepared which was similar to treatment number 6, above, except that cade oil and alpha-ionol were not mixed together, but were added to the opposite ends of the wick. This treatment was prepared by adding 0.6 ml of treatment 1 and 0.6 ml of treatment 2 on opposite ends of the wick. Following treatment, wicks were attached to Jackson traps (Biosys, Inc., Palo Alto, Calif.). Eight traps per treatment were set out in a macadamia nut orchard in a randomized complete block design and approximately 5,000, 10-day old, sterile male *Bactrocera latifrons* fruit flies were released uniformly throughout the trapping grid. Two days after the initial fly release, sticky inserts from the Jackson traps were retrieved and the flies that were trapped were counted. The used sticky inserts were replaced with new inserts, and 5,000 more 10-day old, sterile male *Bactrocera latifrons* were released uniformly throughout the trapping grid. The retrieval of inserts, counting of trapped flies, and replacement of inserts followed by fly release were done after 2 days, then after 5 days, then weekly thereafter to Dec. 26, 1996, with a total of 16 releases and catches. The test was terminated with final insert collection on Jan. 2, 1997.

Figure 2A:
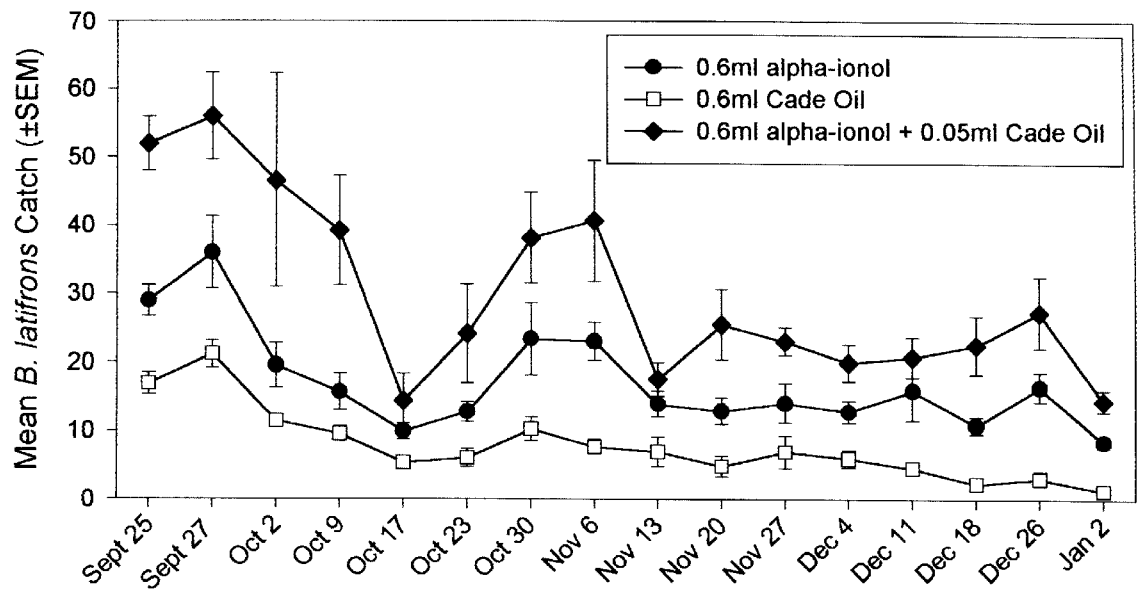
FIGS. 2a–2d and 2f show the mean catch, ± standard error of the mean (SEM), of *Bactrocera latifrons* males at Jackson traps baited with alpha-ionol only, cade oil only, or different volumetric ratio mixtures of alpha-ionol:cade oil. Sticky inserts from the Jackson traps were retrieved at the dates indicated, from Sep. 25, 1996 or Jan. 2, 1997, following release of about 5,000 sterile adult males immediately after insert collection on the previous date. The catches recorded for September 25 were based on flies released on September 23.
Figure 2B:
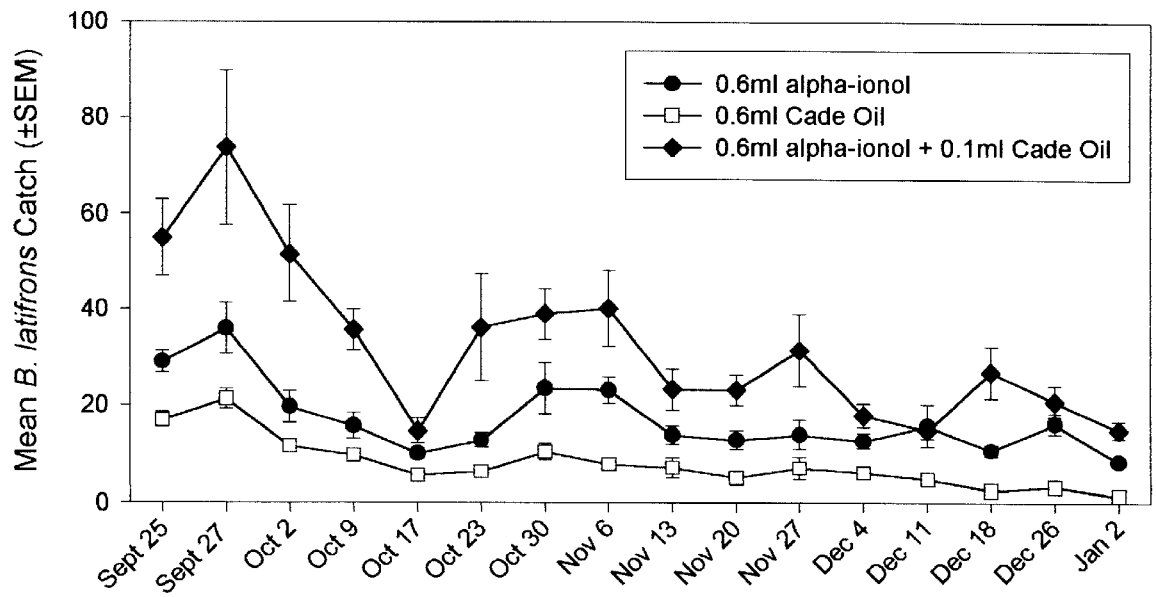
Figure 2C:
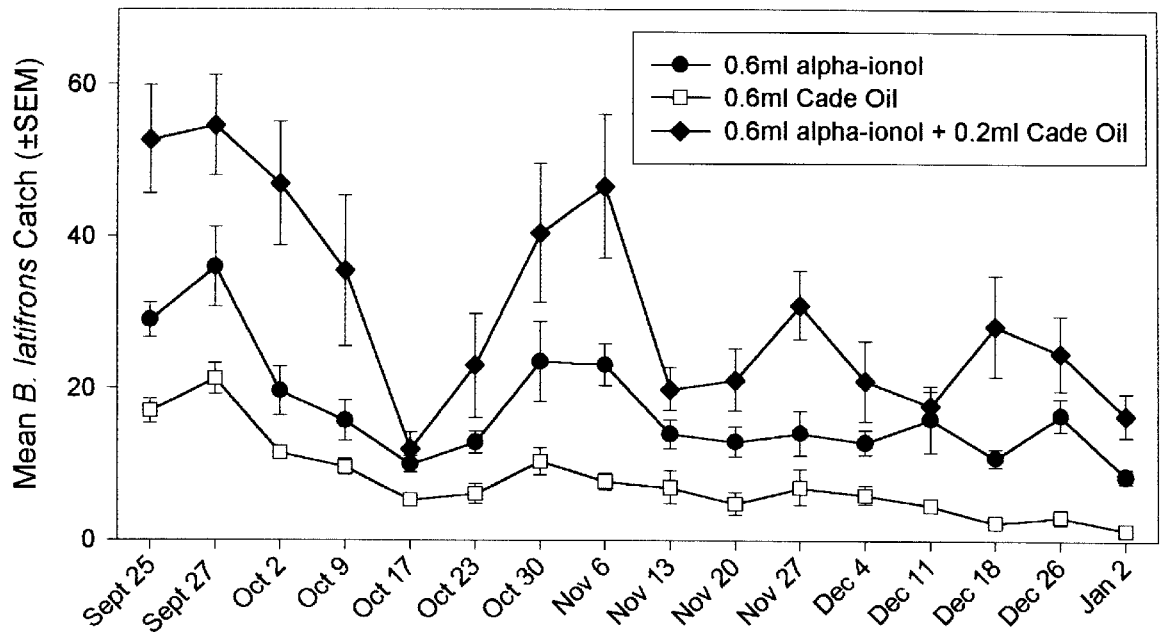
Figure 2D:
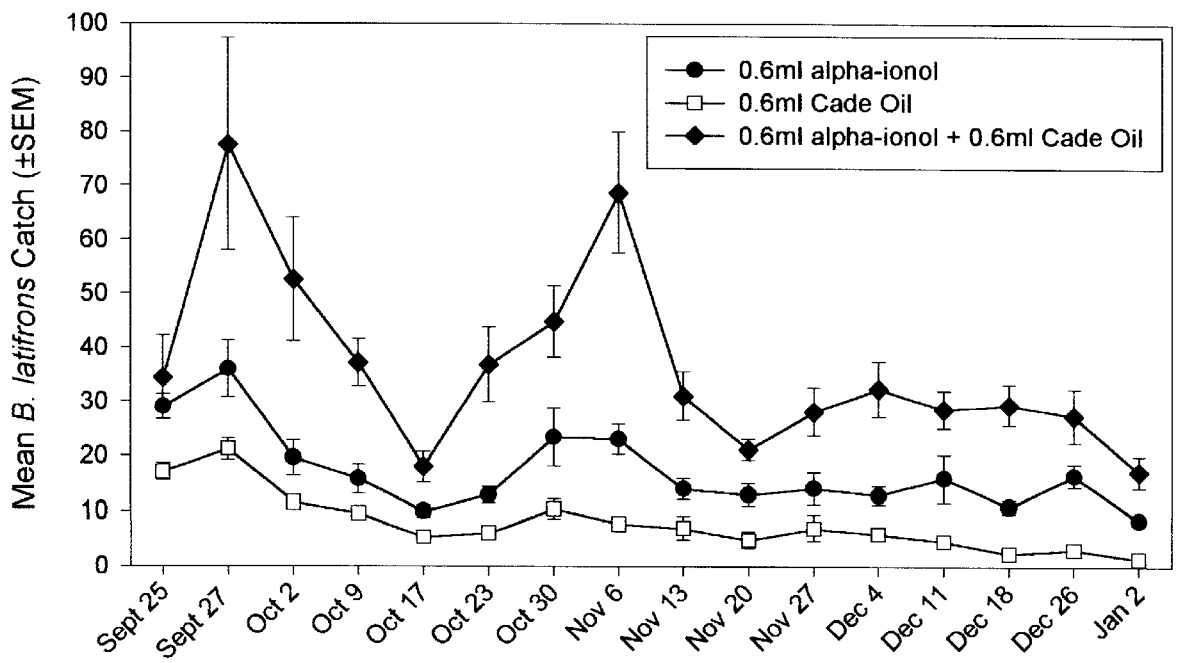
Figure 2E:
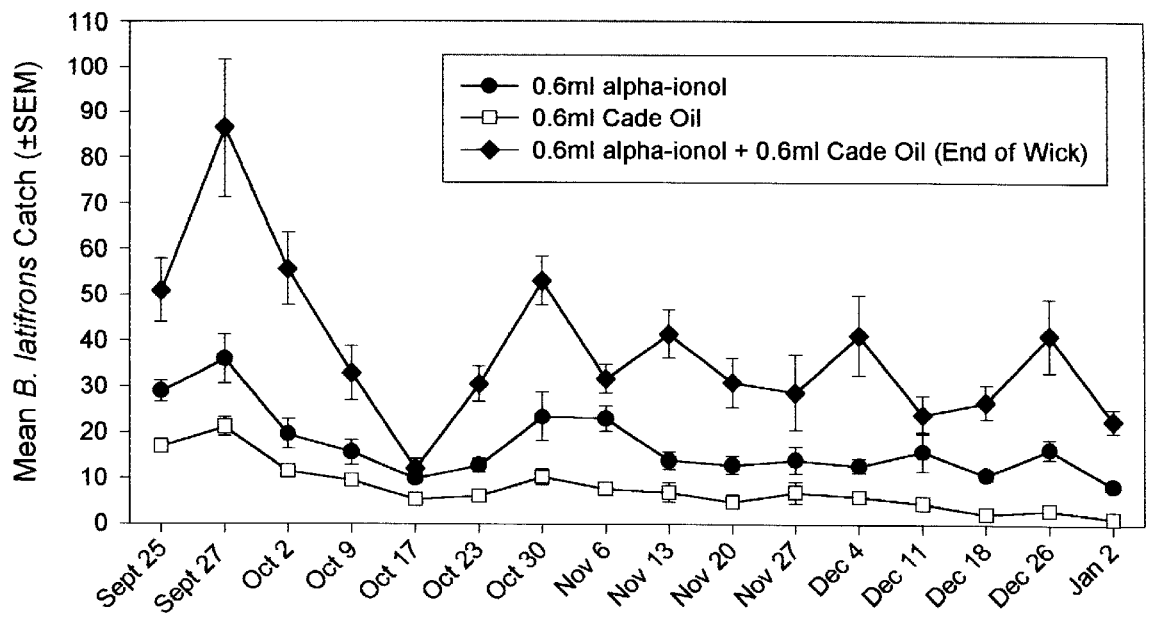
FIG. 2e shows the mean catch, ± standard error of the mean (SEM), of *Bactrocera latifrons* males at Jackson traps baited with alpha-ionol only (0.6 ml), cade oil only (0.6 ml), or a 1:1 combination of alpha-ionol:cade oil with the alpha-ionol and cade oil not mixed together, but added to the opposite ends of the wick (0.6 ml:0.6 ml). Sticky inserts from the Jackson traps were retrieved at the dates indicated, from Sep. 25, 1996 or Jan. 2, 1997, following release of about 5,000 sterile adult males immediately after insert collection on the previous date. The catches recorded for September 25 were based on flies released on September 23.
Figure 2F:
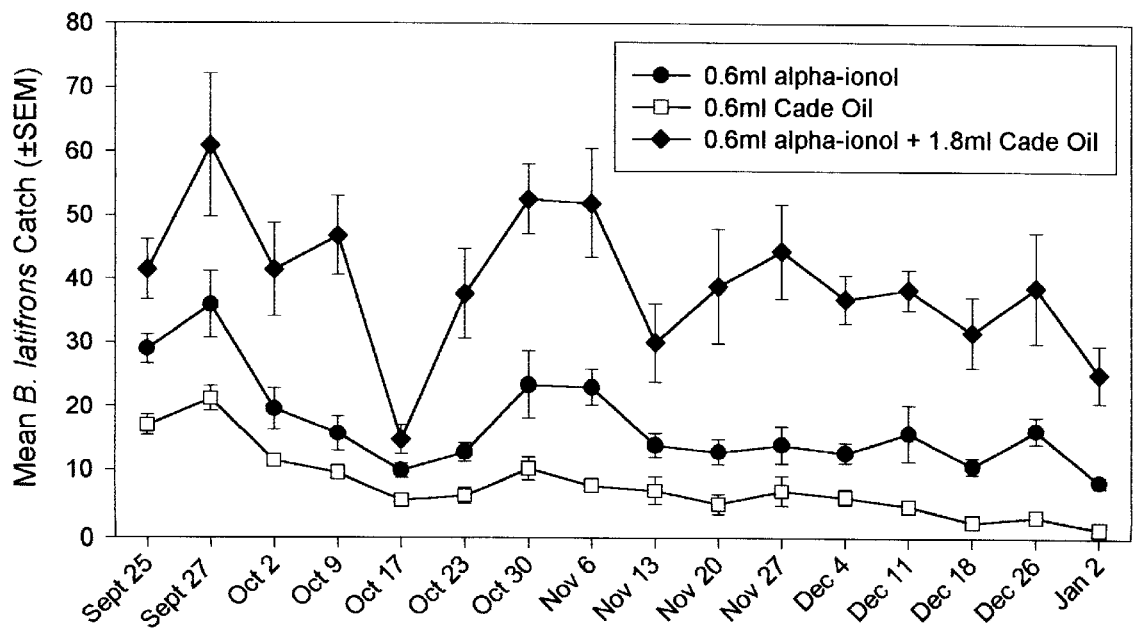
Figure 2G:
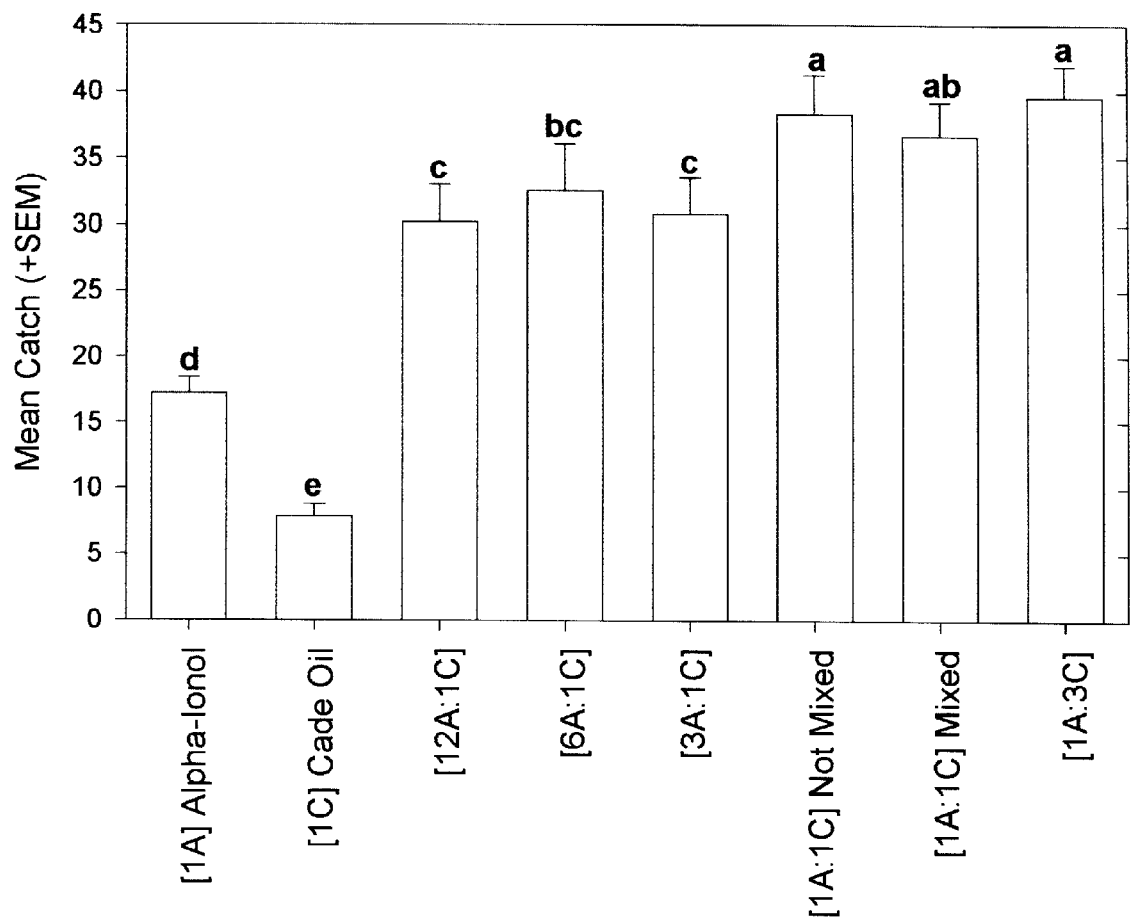
FIG. 2g shows the overall mean catch of *Bactrocera latifrons* males of Jackson traps baited with alpha-ionol only, cade oil only, or the different ratio mixtures or combination of alpha-ionol:cade oil, as described in FIGS. 2a–2f. Letters above the columns of treatment means indicate significance of difference from other treatment means (based on Waller-Duncan K-ratio T test; alpha=0.05). Columns where the letters are different are significantly different.

Results. Male catch results for all 16 trap collections are presented in FIGS. 2a–2g. For analysis purposes, trap catches were combined for collections 1–4 (Period 1), 5–8 (Period 2), 9–12 (Period 3), and 13–16 (Period 4). There was a significant difference in catch both among treatments (F=30.49; df=7,245; P<0.0001) and among time periods (F=48.34; df=3,245; P<0.0001). Catch in the cade oil only treatment was significantly less than in the alpha-ionol only treatment. Catch in all of the alpha-ionol+cade oil treatments was significantly greater than both the alpha-ionol alone and cade oil alone treatments (see FIG. 2g). There was no significant difference in mean catch between the treatment where alpha-ionol and cade oil were mixed together in a 1:1 mix and the treatment where alpha-ionol and cade oil were applied to opposite ends of the wick. Significance of difference of mean catch among Periods was as follows: Period 1 (43.1)>Period 2 (28.8)>Period 3 (23.8)=Period 4 (20.8). This trend suggests reduced catch over time concurrent with the weathering of the wick which is as would be expected.

The results presented here clearly show the synergistic effects of alpha-ionol plus cade oil. This synergistic effect occurs with even small additions of cade oil.

Example 3

The following example describes field tests assessing the attractancy of alpha-ionol alone, cade oil alone, and the invention (alpha-ionol plus cade oil).

Materials and Methods. On Nov. 14, 1996, cotton wicks (3.8 cm long by 1.0 cm diameter) were treated with mixtures prepared with different proportions of alpha-ionol (Bedoukian Research, Inc., Danbury, Conn.) and cade oil (Penta International Corporation, Livingston, N.J.). The knockdown pesticide, dibrom (Dibrom Concentrate, Valent USA Corporation, Walnut Creek, Cailf.; ingredient name: naled), was added to each mixture so that each treated wick would have at least 0.1 ml dibrom. The following proportions (alpha-ionol:cade oil) were prepared, with quantity added to individual wicks also indicated:

(1) [0:1] 0.6 ml cade oil+0.1 ml dibrom;
(2) [1:0] 0.6 ml alpha-ionol+0.1 ml dibrom;
(3) [6:1] 0.6 ml alpha-ionol+0.1 ml cade oil+0.1 ml dibrom;
(4) [3:1] 0.6 ml alpha-ionol+0.2 ml cade oil+0.1 ml dibrom;
(5) [1:1] 0.6 ml alpha-ionol+0.6 ml cade oil+0.1 ml dibrom;
(6) [1:3] 0.6 ml alpha-ionol+1.8 ml cade oil+0.1 ml dibrom.

In addition to these six treatments, a seventh treatment was prepared which was similar to treatment number 5, above, except that cade oil and alpha-ionol were not mixed together, but were added to the opposite ends of the wick. This treatment was prepared by adding 0.6 ml of treatment 1 and 0.6 ml of treatment 2 on opposite ends of the wick. Following treatment, wicks were attached to Jackson traps (Biosys, Inc., Palo Alto, Cailf.). Eight traps per treatment were set out in a macadamia nut orchard in a randomized complete block design and approximately 5,000, 10-day old, sterile male *Bactrocera latifrons* fruit flies were released uniformly throughout the trapping grid. Four days after the initial fly release, sticky inserts from the Jackson traps were retrieved and the flies that were trapped were counted. The used sticky inserts were replaced with new inserts, and 5,000 more 10-day old, sterile male *Bactrocera latifrons* were released uniformly throughout the trapping grid. The retrieval of inserts, counting of trapped flies, and replacement of inserts followed by fly release were done weekly thereafter to Mar. 3, 1997. The test was terminated with final insert collection on Mar. 10, 1997.

Figure 3A:
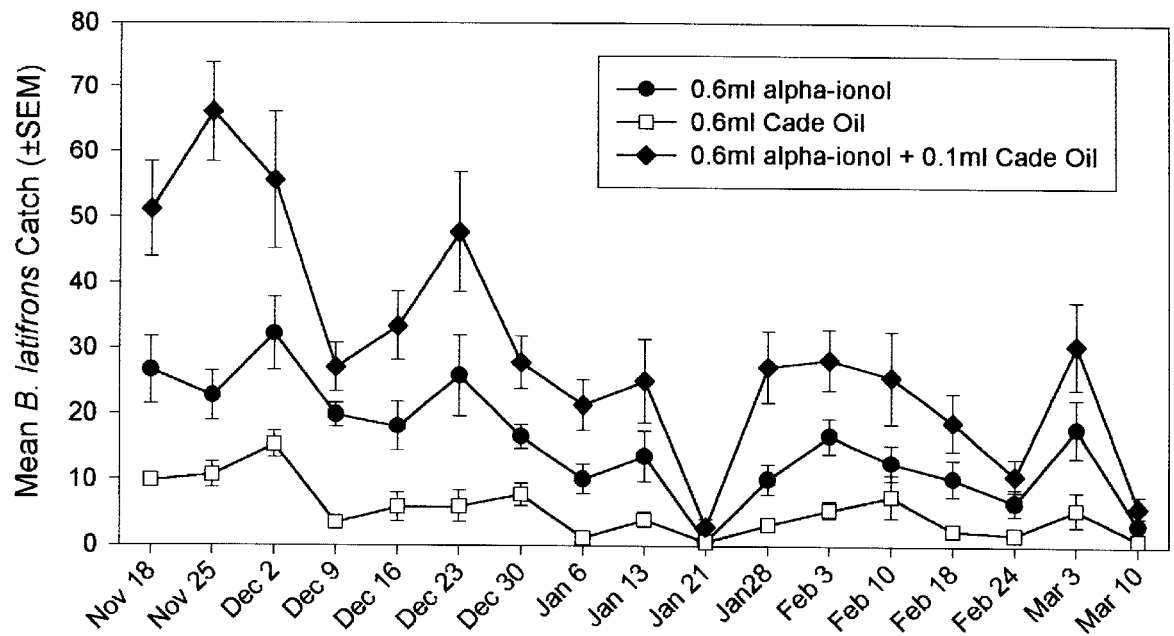
FIGS. 3a–3c and 3e show the mean catch, ± standard error of the mean (SEM), of *Bactrocera latifrons* males at Jackson traps baited with alpha-ionol only (0.6 ml), cade oil only (0.6 ml), or different ratio mixtures of alpha-ionol:cade oil. Sticky inserts from the Jackson traps were retrieved at the dates indicated, from Nov. 18, 1996 to Mar. 10, 1997, following release of about 5,000 sterile adult males immediately after insert collection on the previous date. The catches recorded for November 18 were based on flies released on November 14.
Figure 3B:
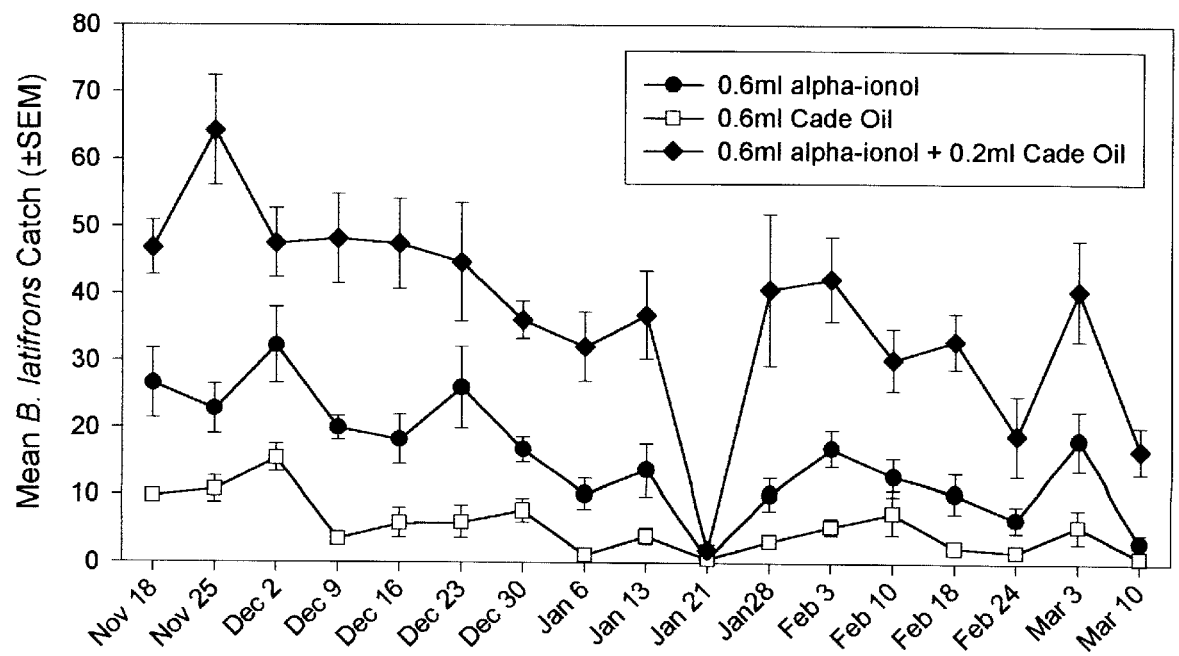
Figure 3C:
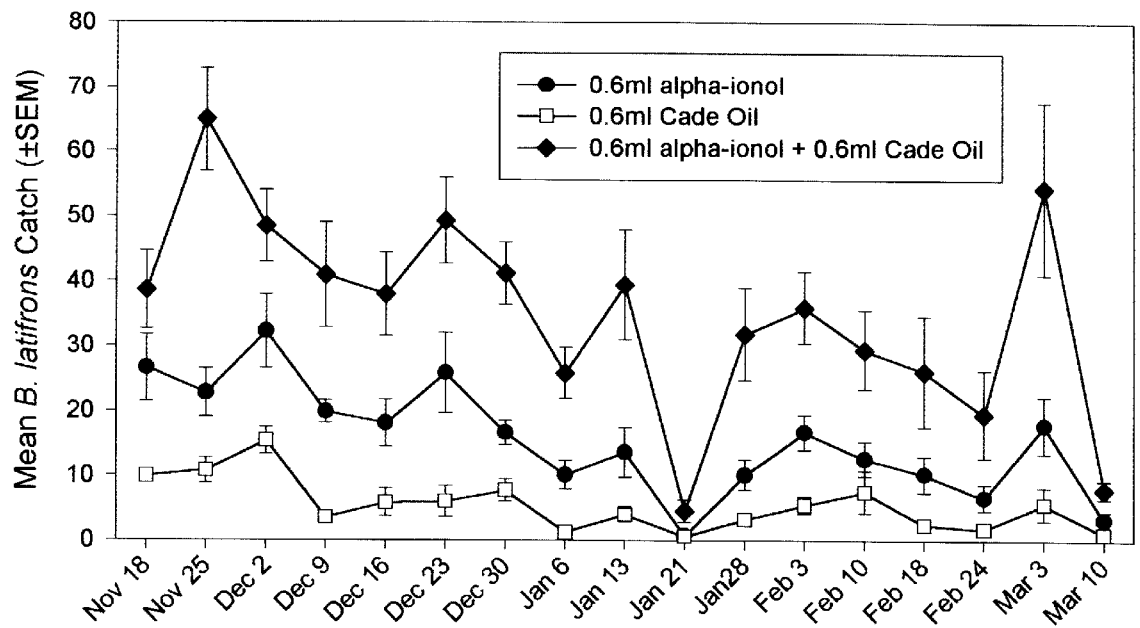
Figure 3D:
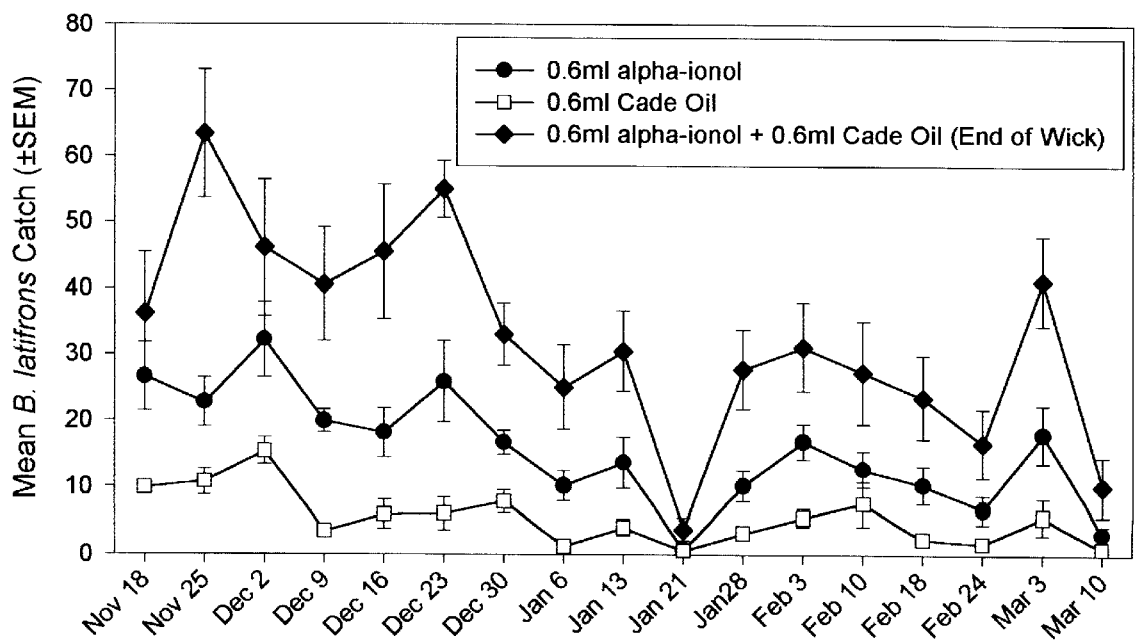
FIG. 3d shows the mean catch, ± standard error of the mean (SEM), of *Bactrocera latifrons* males at Jackson traps baited with alpha-ionol only (0.6 ml), cade oil only (0.6 ml), or a 1:1 combination of alpha-ionol:cade oil with the alpha-ionol and cade oil not mixed together, but added to the opposite ends of the wick (0.6 ml:0.6 ml). Sticky inserts from the Jackson traps were retrieved at the dates indicated, from Nov. 18, 1996 to Mar. 10, 1997, following release of about 5,000 sterile adult males immediately after insert collection on the previous date. The catches recorded for November 18 were based on flies released on November 14.
Figure 3E:
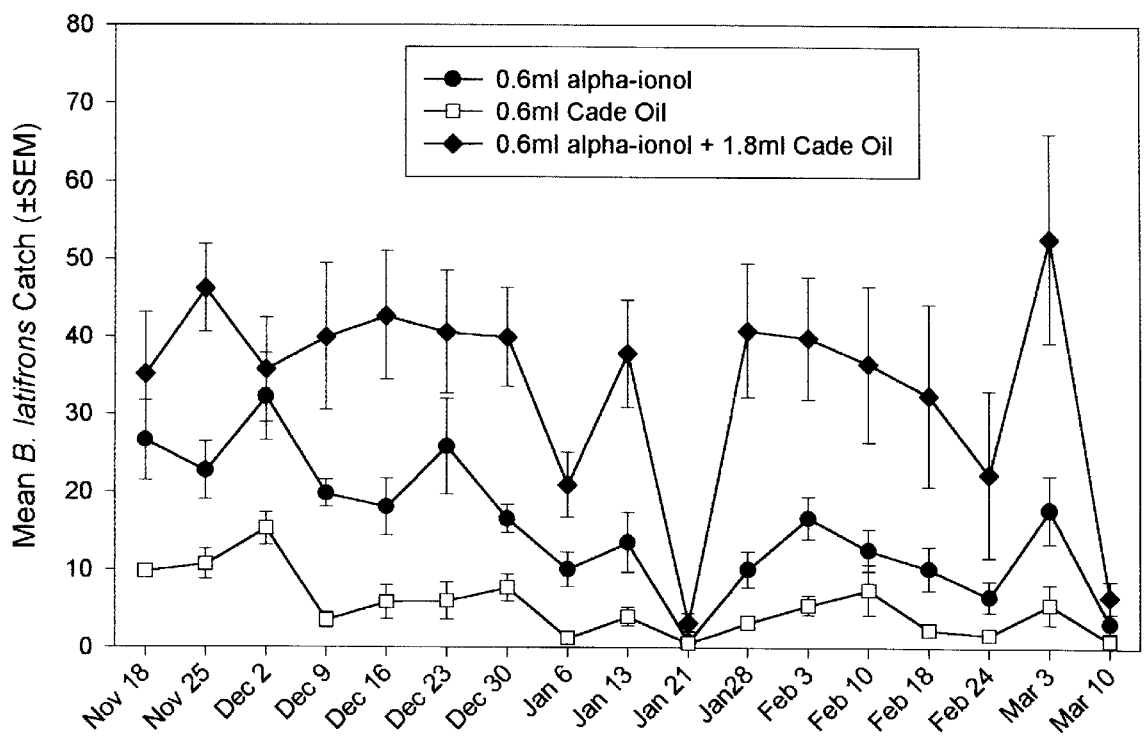
Figure 3F:
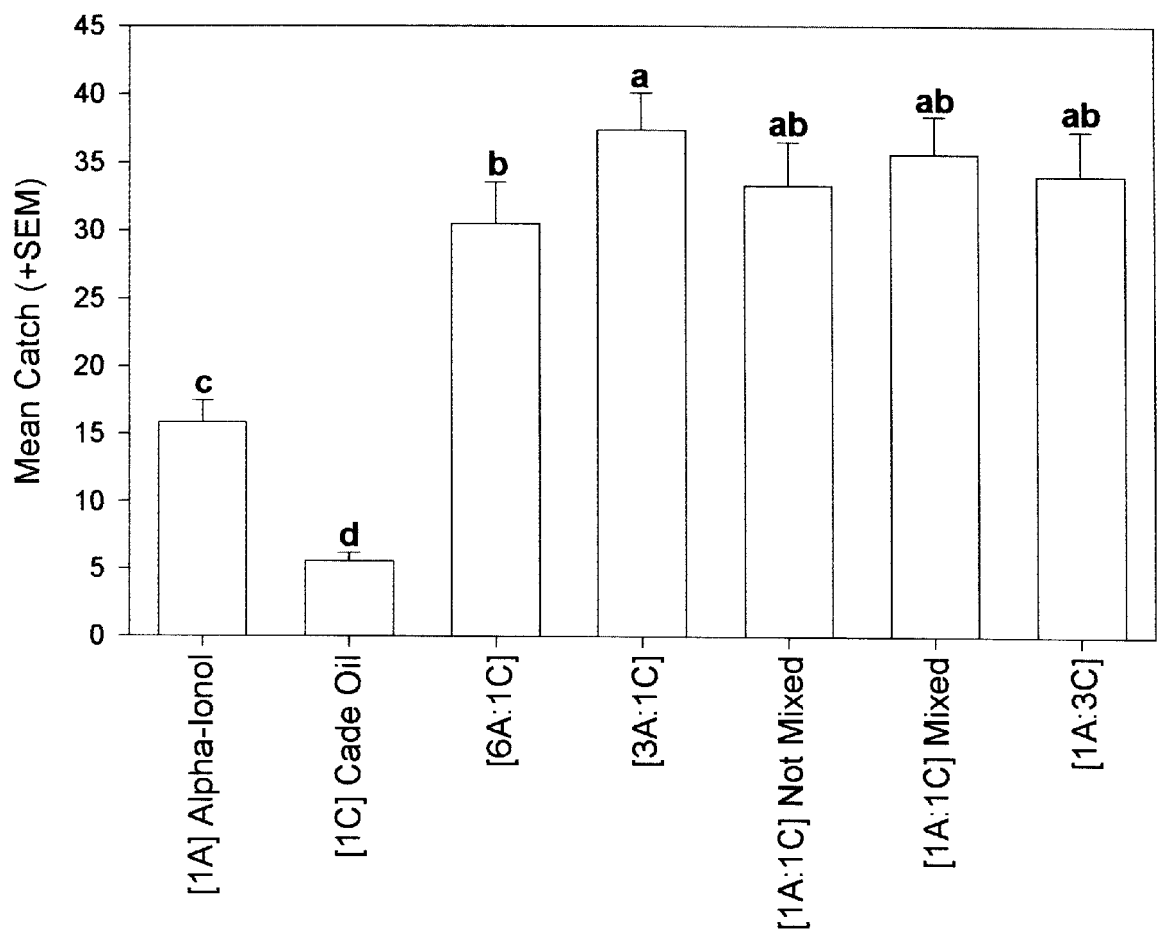
FIG. 3f shows the overall mean catch of *Bactrocera latifrons* males at Jackson traps baited with alpha-ionol only, cade oil only, or different proportions of alpha-ionol:cade oil. Letters above the columns of treatment means indicate significance of difference from other treatment means (based on Waller-Duncan Kratio T test; alpha=0.05). Columns where the letters are different are significantly different.

Results. Male catch results for all 17 trap collections are presented in FIGS. 3a–3e. For analysis purposes, trap catches were combined for collections 1–4 (Period 1), 5–8 (Period 2), 9–12 (Period 3), and 13–17 (Period 4). There was a significant difference in catch both among treatments (F=28.32; df=6,214; P<0.0001) and among time periods (F=26.22; df=3,214; P<0.0001). Catch in the cade oil only treatment was significantly less than in the alpha-ionol only treatment. Catch in the alpha-ionol+cade oil treatments was significantly greater than both the alpha-ionol alone and cade oil alone treatments (see FIG. 3f). There was no significant difference in mean catch between the treatment where alpha-ionol and cade oil were mixed together in a 1:1 mix and the treatment where alpha-ionol and cade oil were applied to opposite ends of the wick. Significance of difference of mean catch among Periods was as follows: Period 1 (38.7)>Period 2 (30.0)>Period 3 (20.9)=Period 4 (20.). This trend suggests reduced catch over time concurrent with the weathering of the wick which is as would be expected.

The results presented here clearly show the synergistic effects of alpha-ionol plus cade oil. This synergistic effect occurs with even small additions of cade oil.

It is understood that the foregoing detailed description is given merely by way of illustration and that modification and variations may be made within, without departing from the spirit and scope of the invention.

What is claimed is:

1. An attractant composition for male *Bactrocera latifrons* (Hendel) fruit flies, which comprises a mixture of alpha-ionol and cade oil.

2. The composition of claim 1 wherein the mixture of alpha-ionol and cade oil comprises a volumetric ratio range of about 12:1 to 1:3 alpha-ionol:cade oil.

3. A lure for attracting *Bactrocera latifrons* (Hendel) fruit flies, which comprises a dispenser means which contains alpha-ionol and cade oil.

4. The lure of claim 3 wherein said dispenser means contains a mixture alpha-ionol and cade oil.

5. The lure of claim 3 wherein said dispenser means comprises one or more dispensers wherein alpha-ionol and cade oil are separately released in sufficient proximity to provide an effective attractant amount of a vapor blend of alpha-ionol and cade oil.

6. The lure of claim 3 wherein said dispenser means is located within a trapping means for said fruit flies.

7. The lure of claim 3 which further includes a means for controlling *Bactrocera latifrons* fruit flies.

8. A trapping system for detecting, monitoring, attracting or controlling *Bactrocera latifrons* (Hendel) fruit flies, which comprises a dispenser means located within a trapping means which provides an effective attractant amount of alpha-ionol and cade oil.

9. The trapping system of claim 8 wherein said dispenser means contains a mixture of alpha-ionol and cade oil.

10. The trapping system of claim 8 wherein said dispenser means comprises one or more dispensers wherein alpha-ionol and cade oil are separately released in sufficient proximity to provide an effective attractant amount of a vapor blend of alpha-ionol and cade oil.

11. A method for attracting *Bactrocera latifrons* (Hendel) fruit flies, which comprises placing in an area where said fruit flies are to be attracted a dispenser means which provides an effective attractant amount of alpha-ionol and cade oil.

12. The method of claim 11 wherein said dispenser means contains a mixture of alpha-ionol and cade oil.

13. The method of claim 11 wherein said dispenser means comprises one or more dispensers which release alpha-ionol and cade oil to provide an effective attractant amount of a vapor blend of alpha-ionol and cade oil.

14. The method of claim 11 which further includes a means for controlling *Bactrocera latifrons* fruit flies.

* * * * *